US010813595B2

(12) United States Patent
Tsymbalenko et al.

(10) Patent No.: US 10,813,595 B2
(45) Date of Patent: Oct. 27, 2020

(54) FULLY AUTOMATED IMAGE OPTIMIZATION BASED ON AUTOMATED ORGAN RECOGNITION

(71) Applicant: General Electric Company, Schenectady, NY (US)

(72) Inventors: Yelena Viktorovna Tsymbalenko, Mequon, WI (US); Paul O'Dea, Muskego, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 812 days.

(21) Appl. No.: 15/374,321

(22) Filed: Dec. 9, 2016

(65) Prior Publication Data

US 2018/0160981 A1 Jun. 14, 2018

(51) Int. Cl.
| | |
|---|---|
| *A61B 8/00* | (2006.01) |
| *A61B 5/00* | (2006.01) |
| *A61B 8/08* | (2006.01) |
| *G16H 50/20* | (2018.01) |
| *G16H 40/63* | (2018.01) |
| *G16H 50/50* | (2018.01) |
| *G16H 30/40* | (2018.01) |
| *A61B 8/14* | (2006.01) |

(52) U.S. Cl.
CPC ............ *A61B 5/7264* (2013.01); *A61B 5/743* (2013.01); *A61B 8/5207* (2013.01); *A61B 8/5215* (2013.01); *A61B 8/585* (2013.01); *G16H 30/40* (2018.01); *G16H 40/63* (2018.01); *G16H 50/20* (2018.01); *G16H 50/50* (2018.01); *A61B 5/004* (2013.01); *A61B 5/0037* (2013.01); *A61B 8/14* (2013.01); *A61B 8/4444* (2013.01); *A61B 8/461* (2013.01); *A61B 8/5223* (2013.01); *A61B 2576/00* (2013.01)

(58) Field of Classification Search
None
See application file for complete search history.

(56) References Cited

U.S. PATENT DOCUMENTS

| 7,580,554 B2 | 8/2009 | Spahn |
| 7,648,460 B2 | 1/2010 | Simopoulos et al. |
| 8,357,094 B2 | 1/2013 | Mo et al. |
| 8,938,113 B2 | 1/2015 | Kovalan et al. |

(Continued)

*Primary Examiner* — Joel F Brutus
(74) *Attorney, Agent, or Firm* — McAndrews, Held & Malloy, Ltd.; Jacob Groethe; David Bates

(57) ABSTRACT

Systems and methods are provided for fully automated image optimization based on automated organ recognition. In medical imaging systems, during medical imaging based on a particular imaging technique, an anatomical feature in an area being imaged may be automatically identifying, and based on the identifying of the anatomical feature, one or more imaging parameters or settings for optimizing imaging quality for the identified anatomical feature may be automatically determined. Imaging functions may then be configured based on the determined one or more imaging parameters or settings, and, based on processing of medical imaging dataset acquired based on that configuration, one or more medical images for rendering. A deep learning and/or neural network based model may be used in identifying the anatomical feature and selecting the one or more imaging parameters or settings.

20 Claims, 4 Drawing Sheets

(56) References Cited

U.S. PATENT DOCUMENTS

| | | | |
|---|---|---|---|
| 2007/0276246 A1* | 11/2007 | Lin | A61B 8/4209 600/444 |
| 2008/0097942 A1 | 4/2008 | Zhao et al. | |
| 2014/0221838 A1* | 8/2014 | Loupas | G01S 15/8984 600/454 |
| 2016/0157831 A1* | 6/2016 | Kang | A61B 8/5223 600/443 |
| 2016/0174902 A1* | 6/2016 | Georgescu | G06T 7/73 600/408 |

* cited by examiner

FULLY AUTOMATED IMAGE OPTIMIZATION BASED ON AUTOMATED ORGAN RECOGNITION

FIELD

Aspects of the present disclosure relate to medical imaging. More specifically, certain embodiments relate to methods and systems for fully automated image optimization based on automated organ recognition.

BACKGROUND

Various medical imaging techniques may be used, such as in imaging organs and soft tissues in a human body. Examples of medical imaging techniques include ultrasound imaging, computed tomography (CT) scans, magnetic resonance imaging (MRI), etc. The manner by which images are generated during medical imaging depends on the particular technique.

For example, ultrasound imaging uses real time, non-invasive high frequency sound waves to produce ultrasound images, typically of organs, tissues, objects (e.g., fetus) inside the human body. Images produced or generated during medical imaging may be two-dimensional (2D), three-dimensional (3D), and/or four-dimensional (4D) images (essentially real-time/continuous 3D images). During medical imaging, imaging datasets (including, e.g., volumetric imaging datasets during 3D/4D imaging) are acquired and used in generating and rendering corresponding images (e.g., via a display) in real-time.

Various issues may exist with conventional approaches for optimizing medical imaging. In this regard, conventional systems and methods, if any existed, for optimizing image quality during medical imaging operations, can be inefficient and/or ineffective.

Further limitations and disadvantages of conventional and traditional approaches will become apparent to one of skill in the art, through comparison of such systems with some aspects of the present disclosure, as set forth in the remainder of the present application with reference to the drawings.

BRIEF SUMMARY

System and methods are provided for a fully automated image optimization based on automated organ recognition, substantially as shown in and/or described in connection with at least one of the figures, as set forth more completely in the claims.

These and other advantages, aspects and novel features of the present disclosure, as well as details of one or more illustrated example embodiments thereof, will be more fully understood from the following description and drawings.

DETAILED DESCRIPTION

Figure 1:
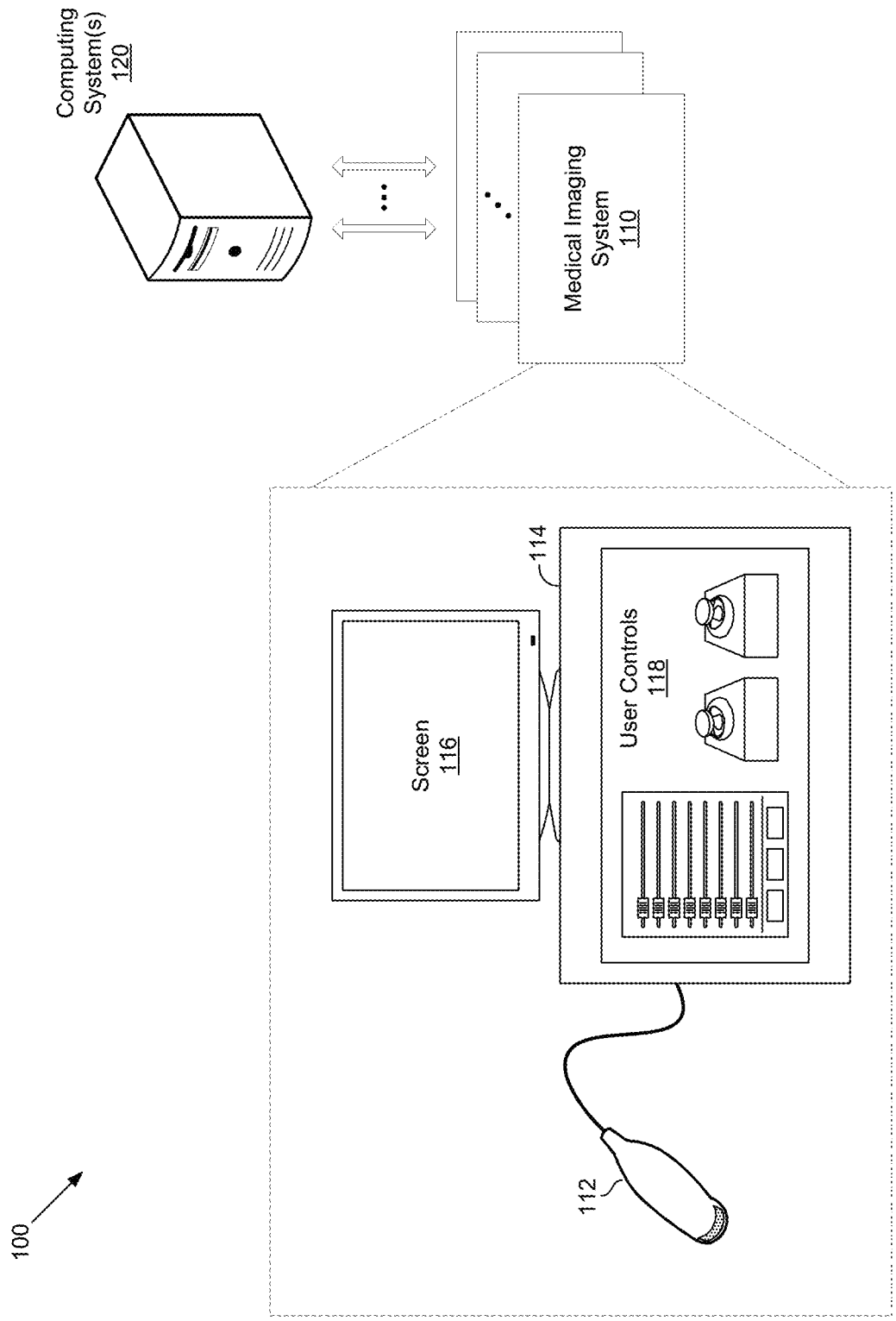
FIG. 1 is a block diagram illustrating an example medical imaging arrangement that supports fully automated image optimization based on automated organ recognition, in accordance with the present disclosure.

Various implementations in accordance with the present disclosure may be directed to fully automated image optimization based on automated organ recognition. An example method in accordance with the present disclosure may comprise, in an medical imaging device: automatically identifying (e.g., without requiring any input by the user), during medical imaging based on a particular imaging technique, an anatomical feature in an area being imaged; automatically determining (e.g., without requiring any input by the user), based on the identifying of the anatomical feature, one or more imaging parameters or settings for optimizing imaging quality for the identified anatomical feature; configuring imaging functions in the medical imaging device based on the determined one or more imaging parameters or settings; acquiring based on the configuration, medical imaging dataset corresponding to the area being imaged; and generating, based on processing of the medical imaging dataset, one or more medical images for rendering. The particular imaging technique comprises ultrasound imaging; and the medical imaging dataset is acquired using captured echo ultrasound signals.

In an example implementation, a deep learning and/or neural network based model may be used in identifying the anatomical feature and selecting the one or more imaging parameters or settings. The deep learning and/or neural network based model may be pre-trained for recognizing one or more anatomical features. The deep learning and/or neural network based model may be pre-trained for selecting, for each recognized anatomical feature, one or more imaging optimization parameters or settings. The deep learning and/or neural network based model may be generated and/or updated based on feedback data from one or more users, the feedback data relating to recognizing and/or optimizing imaging for particular anatomical features.

In an example implementation, at least some of the feedback data may be collected and processed in a dedicated computing system. The deep learning and/or neural network based model and/or updates to the deep learning and/or neural network based model may be imported from the dedicated computing system to the medical imaging device.

In an example implementation, handling of user input and/or output, during the medical imaging, based on the identifying of the anatomical feature.

In an example implementation, incorporating into the generated one or more images, based on the identifying of the anatomical feature, information relating to the anatomical feature.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments. The following detailed description is, therefore, not to be taken in a limiting sense, and the scope of the present invention is defined by the appended claims and their equivalents.

An example system in accordance with the present disclosure may comprise a probe that is operable to acquire medical imaging data; a control component that comprises processing circuitry; and an input/output component for outputting medical images. The processing circuitry is operable to automatically identify (e.g., without requiring any input by the user), during medical imaging based on a particular imaging technique, an anatomical feature in an area being imaged; automatically determine (e.g., without requiring any input by the user), based on the identifying of the anatomical feature, one or more imaging parameters or settings for optimizing imaging quality for the identified anatomical feature; configure imaging related functions in the system based on the determined one or more imaging parameters or settings; and generate, based on processing on medical imaging dataset acquired via the probe, one or more medical images for rendering via the input/output component. The particular imaging technique comprises ultrasound imaging; and the medical imaging dataset is acquired using captured echo ultrasound signals.

In an example implementation, the system may be operable to identify the anatomical feature and determine the one or more imaging parameters or settings using a deep learning and/or neural network based model. The deep learning and/or neural network based model is pre-trained for recognizing one or more anatomical features. The deep learning and/or neural network based model is pre-trained for selecting, for each recognized anatomical feature, one or more imaging optimization parameters or settings. The deep learning and/or neural network based model is configured and/or updated based on feedback data from one or more users, the feedback data relating to recognizing and/or optimizing imaging for particular anatomical features. The deep learning and/or neural network based model and/or updates to the deep learning and/or neural network based model are imported into the system.

In an example implementation, the system may be operable to handle of user input and/or output, during the medical imaging, based on the identifying of the anatomical feature.

In an example implementation, the system may be operable to incorporate into the generated one or more images, based on the identifying of the anatomical feature, information relating to the anatomical feature.

An example non-transitory computer readable medium, in accordance with the present disclosure, may have stored thereon a computer program having at least one code section, the at least one code section being executable by a machine for causing the machine to perform one or more steps comprising: automatically identifying (e.g., without requiring any input by the user), during medical imaging based on a particular imaging technique, an anatomical feature in an area being imaged based on a deep learning and/or neural network based model; automatically determining (e.g., without requiring any input by the user), based on the identifying of the anatomical feature, and using the deep learning and/or neural network based model, one or more imaging parameters or settings for optimizing imaging quality for the identified anatomical feature; configuring operations and/or function relating to the medical imaging based on the determined one or more imaging parameters or settings; acquiring based on the configuration, medical imaging datasets corresponding to the area being imaged; and generating, based on processing on the medical imaging datasets, one or more medical images for rendering.

As used herein, an element or step recited in the singular and proceeded with the word "a" or "an" should be understood as not excluding plural of said elements or steps, unless such exclusion is explicitly stated. Furthermore, references to "an embodiment," "one embodiment," "a representative embodiment," "an example embodiment," "various embodiments," "certain embodiments," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

In addition, as used herein, the phrase "pixel" also includes embodiments where the data is represented by a "voxel." Thus, both the terms "pixel" and "voxel" may be used interchangeably throughout this document.

Also as used herein, the term "image" broadly refers to both viewable images and data representing a viewable image. However, many embodiments generate (or are configured to generate) at least one viewable image. Further, with respect to ultrasound imaging, as used herein the phrase "image" is used to refer to an ultrasound mode such as B-mode, CF-mode and/or sub-modes of CF such as TVI, Angio, B-flow, BMI, BMI_Angio, and in some cases also MM, CM, PW, TVD, CW where the "image" and/or "plane" includes a single beam or multiple beams.

Furthermore, the term processor or processing unit, as used herein, refers to any type of processing unit that can carry out the required calculations, such as single or multi-core: CPU, Graphics Board, DSP, FPGA, ASIC, or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams." Also, forming of images may be performed using channel combinations that may originate from more than one transmit event (e.g., synthetic aperture techniques).

In various embodiments, imaging processing, including visualization enhancement, to form images may be performed, for example, in software, firmware, hardware, or a combination thereof.

FIG. 1 is a block diagram illustrating an example medical imaging arrangement that supports fully automated image optimization based on automated organ recognition, in accordance with the present disclosure. Shown in FIG. 1 is an example setup 100 that comprises one or more medical imaging systems 110 and one or more computing systems 120.

The medical imaging system 110 comprise suitable hardware, software, or a combination thereof, for supporting medical imaging—that is enabling obtaining data used in generating and/or rendering images during medical imaging exams. This may entail capturing of particular type of data, in particular manner, which may in turn be used in generating data for the images. For example, the medical imaging system 110 may be an ultrasound system, configured for generating and/or rendering ultrasound images. An example implementation of an ultrasound system that may correspond to the medical imaging system 110 is described in more detail with respect to FIG. 2.

As shown in FIG. 1, the medical imaging system 110 may comprise a probe 112, which may be portable and movable, and a display/control unit 114. The probe 112 may be used in generating and/or capturing particular type of signals (or data corresponding thereto), such as by being moved over a patient's body (or part thereof). For example, where the medical imaging system 110 is an ultrasound system, the probe 112 may emit ultrasound signals and capture echo ultrasound images.

The display/control unit 114 may be used in displaying images (e.g., via a screen 116). Further, the display/control unit 114 may also support user input/output. For example, the display/control unit 114 may provide (e.g., via the screen 116), in addition to the images, user feedback (e.g., information relating to the system, functions thereof, settings thereof, etc.). The display/control unit 114 may also support user input (e.g., via user controls 118), such as to allow controlling of the medical imaging. The user input may be directed to controlling display of images, selecting settings, specifying user preferences, requesting feedback, etc.

Each computing system 120 may comprise suitable circuitry for processing, storing, and/or communication data. The computing system 120 may be dedicated equipment configured particularly for use in conjunction with medical imaging, including in support of fully automated image optimization, or it may be a general purpose computing system (e.g., personal computer, server, etc.) set up and/or configured to perform the operations described hereinafter with respect to the computing system 120. The computing system 120 may be configured to support operations of the medical imaging systems 110, as described below.

In operation, the medical imaging system 110 may be used in generating and presenting (e.g., rendering or displaying) images during medical exams, and/or in supporting user input/output in conjunction therewith. The images may be 2D, 3D, and/or 4D images. The particular operations or functions performed in the medical imaging system 110 to facilitate the generating and/or presenting of images depends on the type of system—that is the manner by which the data corresponding to the images is obtained and/or generated. For example, in ultrasound imaging, the data is based on emitted and echo ultrasound signals, as described in more detail with respect to FIG. 2.

In various implementations, the medical imaging system 110 may support fully automated image optimization based on automated organ recognition. In this regard, in existing solutions obtaining images with best quality for particular anatomical features typically requires a lot of manual labor. For example, during imaging, when scanning particular anatomical features, the user may need to select or adjust various imaging related parameters and/or settings, to ensure producing images of the best possible quality for those anatomical features. If during the scan anatomy is changed (e.g., focus of scan switched from liver to kidneys), the user may need to manually adjust the settings in order to obtain the best image quality for the desired anatomical features as settings optimal for particular anatomical feature (e.g., liver scans) may not be optimal for different anatomical feature (e.g., kidney scans). If the user does not adjust the settings, the resulting images may not be of optimal quality.

Thus, in various implementation in accordance with the present disclosure, image parameters optimization and settings may be continually set automatically to optimize imaging (e.g., ensure constant optimal image quality) and also increase productivity (reducing manual labor, simplifying workflow, increasing ease of use, etc.). The imaging parameters and settings selection may be done automatically and continually based on automatic recognition of scanned anatomy, using enhanced recognition techniques (e.g., deep learning algorithms). In this regard, advanced adaptive processing techniques (e.g., deep learning algorithms, neural networks, etc.) may be used to enable automatically identifying and recognize anatomical features while scanning. Once the anatomical features are recognized the system can automatically switch and use the imaging parameters and/or setting most optimal for obtain the best image quality scan for recognized anatomical features.

For example, the medical imaging system 110 may be configured to use a deep learning and/or neural network based model to automatically (that is, without any or with very minimal input by the user) identify anatomical features in scanned areas and select imaging settings and/or parameters for optimal images of the identified anatomical features. The deep learning and/or neural network based model may be pre-trained. In this regard, the pre-training may comprise determining (and storing) for each anatomical feature identification data (e.g., unique parameters and/or attributes that can be compared against during scans), and optimization data (the imaging parameters and/or settings resulting in optimal image quality, or data that enable determining such parameters and/or settings in real-time).

In some implementations, once anatomical features are identified, and data corresponding to images optimizing scanning of such anatomical features are obtained, medical imaging systems (e.g., the medical imaging system 110) may be configured to incorporate into corresponding images (generated for rendering), information relating to the identified anatomical features. The information may comprise, for example, description of the anatomical features, information relating to the anatomical features, annotations (which may be configurable by the user), etc.

In some implementations, input and/or output operations may be configured based on identification of anatomical features. For example, once anatomical features are identified, and images optimizing scanning of such anatomical features are obtained and rendered, medical imaging systems (e.g., the medical imaging system 110) may be configured to enable the user to interact with the system based on the particular anatomical features. The screen 116 may be configured, e.g., to enable the user perform examination, checks, measurements, etc. that are particularly configured for the anatomical features being scanned.

In some implementations, the automatic identification and optimizing imaging of anatomical features function (e.g., the deep learning and/or neural network based model) may be continually updated and revised. For example, based on user feedback (including, e.g., any adjustments to settings selected based on the current model), the deep learning and/or neural network based model may be updated—e.g., to ensure that the imaging settings are optimal for the user. In some instances, different versions of the automatic identification and optimizing imaging of anatomical features function, corresponding to different users, may be maintained and used during imaging.

In some implementations, various functions and/or operations pertinent to fully automated image optimization based on automated organ recognition may be offloaded from the imaging systems. This may be done to streamline and/or centralize certain aspects of the processing, to reduce cost (by obviating the need to increase processing resources in the imaging systems). For example, the computing systems 120 may be configured for generating and/or updating automatic identification and optimizing imaging of anatomical features functions (e.g., the deep learning and/or neural network based models). In this regard, the computing systems 120 may generate the deep learning and/or neural network based models and perform the necessary training— that is creating data required for recognizing particular anatomical features, and setting for each anatomical feature corresponding optimization imaging parameters and/or settings.

The computing systems 120 may be set up and/or arranged for use in different ways. For example, in some implementations a single computing system 120 may be used; in other implementations multiple computing systems 120, either configured to work together (e.g., based on distributed-processing configuration), or separately, with each computing system 120 being configured to handle particular aspects and/or functions, and/or to process data for generating model only for particular medical imaging systems 110. In some implementations, the computing systems 120 may be local (e.g., co-located with one or more medical imaging systems 110, such within the same facility and/or same local network); in other implementations, the computing systems 120 may be remote and thus can only be accessed via remote connections (e.g., via the Internet or other available remote access techniques). In a particular implementation, the computing systems 120 may be configured in Cloud-like manner, and may be accessed and/or used in substantially similar way that other Cloud-based systems are accessed and used.

Once data (e.g., anatomical feature recognition models) is generated and/or configured, the data may be copied and/or loaded into the medical imaging systems 110. This may be done in different ways. For example, the models may be loaded via directed connections or links between the medical imaging systems 110 and the computing system 120. In this regard, communications between the different elements in the setup 100 may be done using available wired and/or wireless connections, and/or in accordance any suitable communication (and/or networking) standards or protocols. Alternatively, or additionally, the models may be loaded into the medical imaging systems 110 indirectly. For example, the models may be stored into suitable machine readable media (e.g., flash card, etc.), which are then used to load the models into the medical imaging systems 110 (on-site, such as by users of the systems or authorized personnel), or the models may be downloaded into local communication-capable electronic devices (e.g., laptops, etc.), which are then used on-site (e.g., by users of the systems or authorized personnel) to upload the models into the medical imaging systems 110, via direct connections (e.g., USB connector, etc.).

In some implementations, the automatic identification and optimizing imaging of anatomical features functions (e.g., the deep learning and/or neural network based models) may be generated, updated, and revised based on data obtained from particular users. For example, a number users may be selected (e.g., being deemed "experts") and data obtained from those users (e.g., generated images and/or datasets corresponding thereto) may be used in generating the automatic identification and optimizing imaging of anatomical features functions. Thus, data used in recognizing anatomical features and/or optimizing imaging of these anatomical features may be, for example, set and/or updated based on the data used by those users in obtaining their images (e.g., settings and/or parameters used by those users when anatomical features are focused on, on and/or when images of the anatomical features are deemed of optimal quality). The "experts" users may be (re-)selected regularly. Further, different sets of "expert" users may be used (e.g., for different regions, types of scans, etc.).

Figure 2:
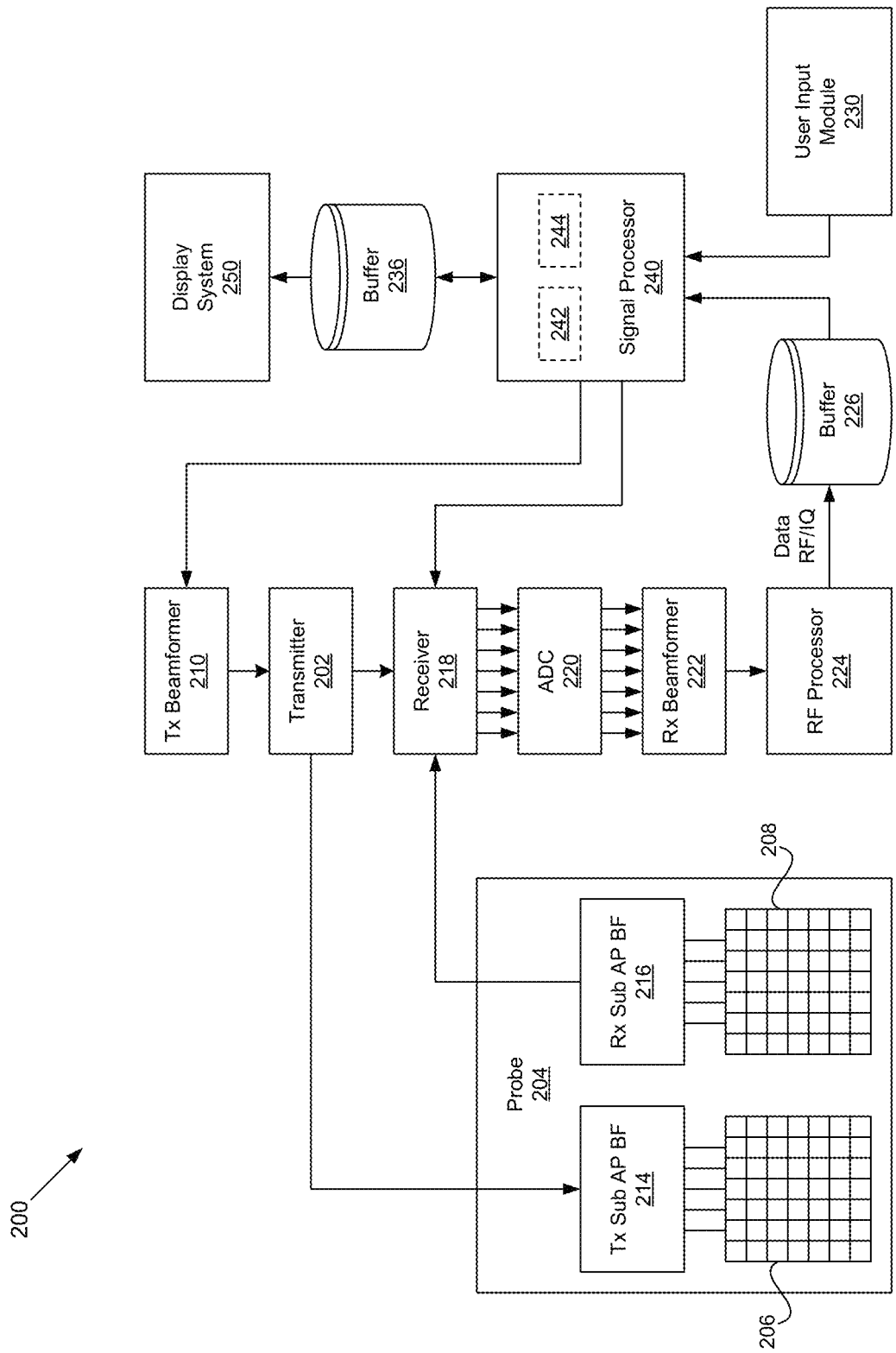
FIG. 2 is a block diagram illustrating an example ultrasound that supports fully automated image optimization based on automated organ recognition, in accordance with the present disclosure.

FIG. 2 is a block diagram illustrating an example ultrasound that supports fully automated image optimization based on automated organ recognition, in accordance with the present disclosure. Shown in FIG. 2 is an ultrasound system 200.

The ultrasound system 200 may comprise suitable components (physical devices, circuitry, etc.) for providing ultrasound imaging. The ultrasound system 200 may correspond to the medical imaging system 110 of FIG. 1 in ultrasound imaging use scenarios. The ultrasound system 200 comprises, for example, a transmitter 202, an ultrasound probe 204, a transmit beamformer 210, a receiver 218, a receive beamformer 222, a RF processor 224, a RF/IQ buffer 226, a user input module 230, a signal processor 240, an image buffer 236, and a display system 250.

The transmitter 202 may comprise suitable circuitry that may be operable to drive an ultrasound probe 204. The transmitter 202 and the ultrasound probe 204 may be implemented and/or configured for one-dimensional (1D), two-dimensional (2D), three-dimensional (3D), and/or four-dimensional (4D) ultrasound scanning. The ultrasound probe 204 may comprise a one-dimensional (1D, 2.25D, 2.5D or 2.75D) array or a two-dimensional (2D) array of piezoelectric elements. For example, as shown in FIG. 2, the ultrasound probe 204 may comprise a group of transmit transducer elements 206 and a group of receive transducer elements 208, that normally constitute the same elements. The transmitter 202 may be driven by the transmit beamformer 210.

The transmit beamformer 210 may comprise suitable circuitry that may be operable to control the transmitter 202 which, through a transmit sub-aperture beamformer 214, drives the group of transmit transducer elements 206 to emit ultrasonic transmit signals into a region of interest (e.g., human, animal, underground cavity, physical structure and the like). In this regard, the group of transmit transducer elements 206 can be activated to transmit ultrasonic signals. The ultrasonic signals may comprise, for example, pulse sequences that are fired repeatedly at a pulse repetition frequency (PRF), which may typically be in the kilohertz range. The pulse sequences may be focused at the same transmit focal position with the same transmit characteristics. A series of transmit firings focused at the same transmit focal position may be referred to as a "packet."

The transmitted ultrasonic signals may be back-scattered from structures in the object of interest, like tissue, to produce echoes. The echoes are received by the receive transducer elements 208. The group of receive transducer elements 208 in the ultrasound probe 204 may be operable to convert the received echoes into analog signals, undergo sub-aperture beamforming by a receive sub-aperture beamformer 216 and are then communicated to the receiver 218.

The receiver 218 may comprise suitable circuitry that may be operable to receive and demodulate the signals from the probe transducer elements or receive sub-aperture beamformer 216. The demodulated analog signals may be communicated to one or more of the plurality of A/D converters (ADCs) 220.

Each plurality of A/D converters 220 may comprise suitable circuitry that may be operable to convert analog signals to corresponding digital signals. In this regard, the plurality of A/D converters 220 may be configured to convert demodulated analog signals from the receiver 218 to corresponding digital signals. The plurality of A/D converters 220 are disposed between the receiver 218 and the receive beamformer 222. Notwithstanding, the disclosure is not limited in this regard. Accordingly, in some embodiments, the plurality of A/D converters 220 may be integrated within the receiver 218.

The receive beamformer 222 may comprise suitable circuitry that may be operable to perform digital beamforming processing to, for example, sum the delayed channel signals received from the plurality of A/D converters 220 and output a beam summed signal. The resulting processed information may be converted back to corresponding RF signals. The corresponding output RF signals that are output from the receive beamformer 222 may be communicated to the RF processor 224. In accordance with some embodiments, the receiver 218, the plurality of A/D converters 220, and the beamformer 222 may be integrated into a single beamformer, which may be digital.

The RF processor 224 may comprise suitable circuitry that may be operable to demodulate the RF signals. In some instances, the RF processor 224 may comprise a complex demodulator (not shown) that is operable to demodulate the RF signals to form In-phase and quadrature (IQ) data pairs (e.g., B-mode data pairs) which may be representative of the corresponding echo signals. The RF (or IQ) signal data may then be communicated to an RF/IQ buffer 226.

The RF/IQ buffer 226 may comprise suitable circuitry that may be operable to provide temporary storage of output of the RF processor 224—e.g., the RF (or IQ) signal data, which is generated by the RF processor 224.

The user input module 230 may comprise suitable circuitry that may be operable to enable obtaining or providing input to the ultrasound system 200, for use in operations thereof. For example, the user input module 230 may be used to input patient data, surgical instrument data, scan parameters, settings, configuration parameters, change scan mode, and the like. In an example embodiment, the user input module 230 may be operable to configure, manage and/or control operation of one or more components and/or modules in the ultrasound system 200. In this regard, the user input module 230 may be operable to configure, manage and/or control operation of transmitter 202, the ultrasound probe 204, the transmit beamformer 210, the receiver 218, the receive beamformer 222, the RF processor 224, the RF/IQ buffer 226, the user input module 230, the signal processor 240, the image buffer 236, and/or the display system 250.

The signal processor 240 may comprise suitable circuitry that may be operable to process the ultrasound scan data (e.g., the RF and/or IQ signal data) and/or to generate corresponding ultrasound images, such as for presentation on the display system 250. The signal processor 240 is operable to perform one or more processing operations according to a plurality of selectable ultrasound modalities on the acquired ultrasound scan data. In some instances, the signal processor 240 may be operable to perform compounding, motion tracking, and/or speckle tracking. Acquired ultrasound scan data may be processed in real-time—e.g., during a B-mode scanning session, as the B-mode echo signals are received. Additionally or alternatively, the ultrasound scan data may be stored temporarily in the RF/IQ buffer 226 during a scanning session and processed in less than real-time in a live or off-line operation.

In operation, the ultrasound system 200 may be used in generating ultrasonic images, including two-dimensional (2D), three-dimensional (3D), and/or four-dimensional (4D) images. In this regard, the ultrasound system 200 may be operable to continuously acquire ultrasound scan data at a particular frame rate, which may be suitable for the imaging situation in question. For example, frame rates may range from 20-70 but may be lower or higher. The acquired ultrasound scan data may be displayed on the display system 250 at a display-rate that can be the same as the frame rate, or slower or faster. An image buffer 236 is included for storing processed frames of acquired ultrasound scan data that are not scheduled to be displayed immediately. Preferably, the image buffer 236 is of sufficient capacity to store at least several seconds' worth of frames of ultrasound scan data. The frames of ultrasound scan data are stored in a manner to facilitate retrieval thereof according to its order or time of acquisition. The image buffer 236 may be embodied as any known data storage medium.

In some instances, the ultrasound system 200 may be configured to support grayscale and color based operations. For example, the signal processor 240 may be operable to perform grayscale B-mode processing and/or color processing. The grayscale B-mode processing may comprise processing B-mode RF signal data or IQ data pairs. For example, the grayscale B-mode processing may enable forming an envelope of the beam-summed receive signal by computing the quantity $(I^2+Q^2)^{1/2}$. The envelope can undergo additional B-mode processing, such as logarithmic compression to form the display data. The display data may be converted to X-Y format for video display. The scan-converted frames can be mapped to grayscale for display. The B-mode frames that are provided to the image buffer 236 and/or the display system 250. The color processing may comprise processing color based RF signal data or IQ data pairs to form frames to overlay on B-mode frames that are provided to the image buffer 236 and/or the display system 250. The grayscale and/or color processing may be adaptively adjusted based on user input—e.g., a selection from the user input module 230, for example, for enhance of grayscale and/or color of particular area.

In some instances, ultrasound imaging may include generation and/or display of volumetric ultrasound images—that is where objects (e.g., organs, tissues, etc.) are displayed three-dimensional 3D. In this regard, with 3D (and similarly 4D) imaging, volumetric ultrasound datasets may be acquired, comprising voxels that correspond to the imaged objects. This may be done, e.g., by transmitting the sound waves at different angles rather than simply transmitting them in one direction (e.g., straight down), and then capture their reflections back. The returning echoes (of transmissions at different angles) are then captured, and processed (e.g., via the signal processor 240) to generate the corresponding volumetric datasets, which may in turn be used (e.g., via a 3D rendering module 242 in the signal processor 240) in creating and/or displaying volume (e.g. 3D) images, such as via the display 250. This may entail use of particular handling techniques to provide the desired 3D perception. For example, volume rendering techniques may be used in displaying projections (e.g., 2D projections) of the volumetric (e.g., 3D) datasets. In this regard, rendering a 2D projection of a 3D dataset may comprise setting or defining a perception angle in space relative to the object being displayed, and then defining or computing necessary information (e.g., opacity and color) for every voxel in the dataset. This may be done, for example, using suitable transfer functions for defining RGBA (red, green, blue, and alpha) value for every voxel.

In some instances, ultrasound imaging may include generation and/or display of volumetric ultrasound images—that is where objects (e.g., organs, tissues, etc.) are displayed three-dimensional 3D. In this regard, with 3D (and similarly 4D) imaging, volumetric ultrasound datasets may be acquired, comprising voxels that correspond to the imaged objects. This may be done, e.g., by transmitting the sound waves at different angles rather than simply transmitting them in one direction (e.g., straight down), and then capture their reflections back. The returning echoes (of transmissions at different angles) are then captured, and processed (e.g., via the signal processor 240) to generate the corresponding volumetric datasets, which may in turn be used (e.g., via a 3D rendering module 242 in the signal processor 240) in creating and/or displaying volume (e.g. 3D) images, such as via the display 250. This may entail use of particular handling techniques to provide the desired 3D perception.

For example, volume rendering techniques may be used in displaying projections (e.g., 2D projections) of the volumetric (e.g., 3D) datasets. In this regard, rendering a 2D projection of a 3D dataset may comprise setting or defining a perception angle in space relative to the object being displayed, and then defining or computing necessary information (e.g., opacity and color) for every voxel in the dataset. This may be done, for example, using suitable transfer functions for defining RGBA (red, green, blue, and alpha) value for every voxel.

In various implementations, the ultrasound system 200 may be configured to support fully automated image optimization based on automated organ recognition. In this regard, the ultrasound system 200 may perform fully automated organ recognition and image optimization substantially as described with respect to the medical imaging system 110 of FIG. 1 (e.g., based on use of deep learning and/or neural network based models) but does so in the context of ultrasound imaging.

Figure 3:
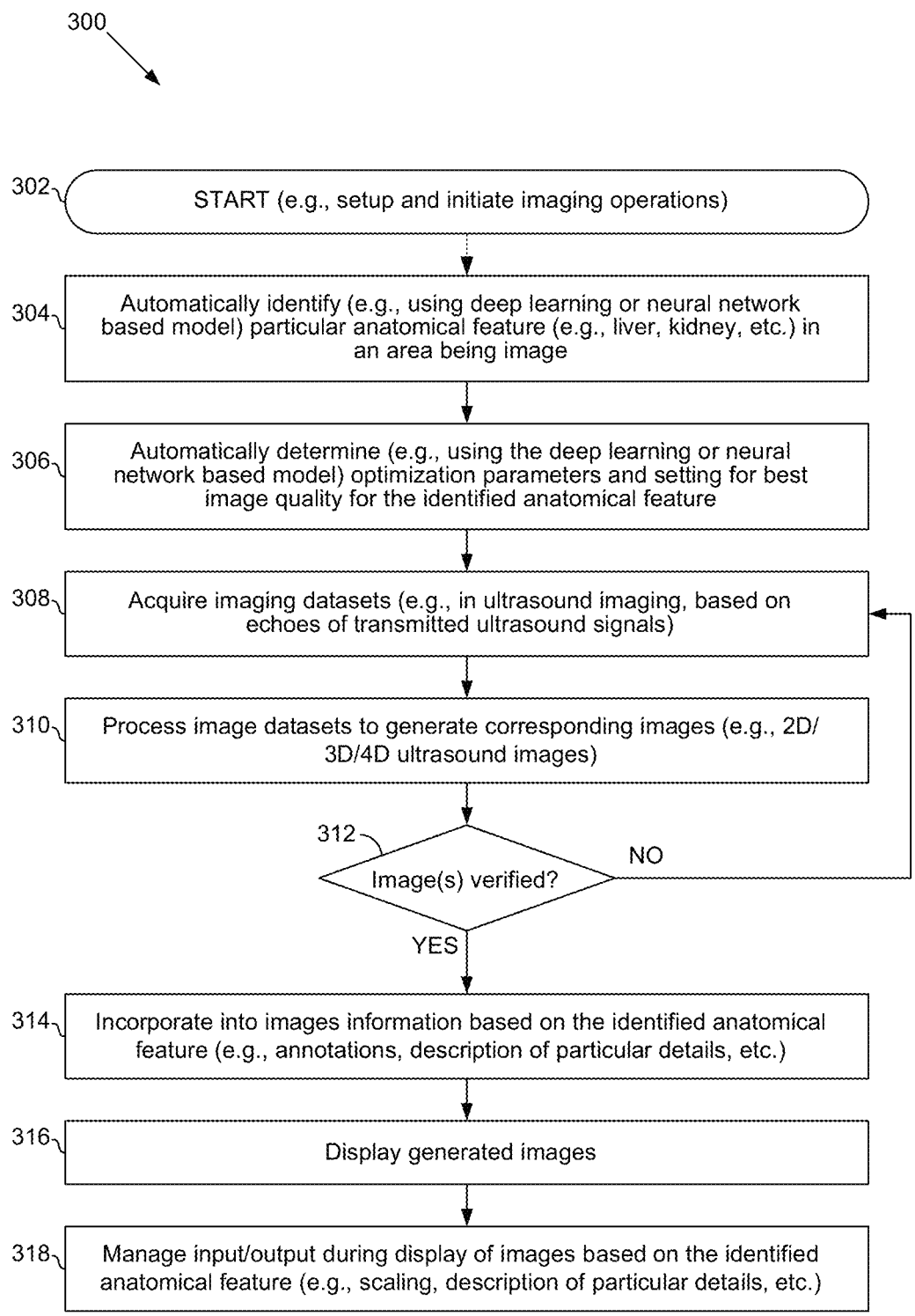
FIG. 3 illustrates a flowchart of an example steps that may be performed for ultrasound imaging with fully automated image optimization based on automated organ recognition.

FIG. 3 illustrates a flowchart of an example steps that may be performed for ultrasound imaging with fully automated image optimization based on automated organ recognition.

Shown in FIG. 3 is flow chart 300, comprising a plurality of example steps (represented as blocks 302-316), which may be performed in a suitable system (e.g., system 200 of FIG. 2) for performing ultrasound imaging with fully automated image optimization based on automated organ recognition.

In start step 302, the system may be setup, and operations may initiate.

In step 304, particular anatomical feature (e.g., liver, kidney, etc.) may be automatically identified (e.g., using deep learning or neural network based model) in an area being imaged.

In step 306, optimization parameters and settings, for best image quality for the identified anatomical feature, may be automatically determined (e.g., using the deep learning or neural network based model).

In step 308, imaging datasets may be acquired (e.g., in ultrasound imaging, based on echoes of transmitted ultrasound signals).

In step 310, the image datasets may be processed to generate corresponding images (e.g., 2D/3D/4D ultrasound images in ultrasound imaging).

In optional step 312, the images may be verified. In this regard, in some instances acquired ultrasound images may be verified, such to confirm that they meet particular conditions or criteria. These conditions or criteria may be based on, for example, particular scanning protocols or standards. For example, the American Institute of Ultrasound in Medicine (AIUM) defines imaging requirements for various types of scans (e.g., for successful scans of liver, abdomen, etc.). In an example implementation, the verification of acquired images may be automatically—e.g., being done using deep learning algorithm/neural network, which may be configured to verify, for the user, that acquired images meet applicable imaging requirements for targeted anatomical features, such as in accordance with particular scanning protocols. In instances where the acquired images are not verified successfully—that is the output of the check done at step 312 is "No", the process may loop back to step 308 (to reacquire the imaging datasets), or alternatively (not shown) the process may exit (e.g., if steps 308-312 are repeated a number of times without successfully acquiring images of the target anatomical features). Otherwise, if the images are verified successfully—that is the output of the check done at step 312 is "Yes", the process may proceed to step 314.

In optional step 314, information (e.g., annotations, description of particular details, etc.) may be incorporated into the generated images based on the identified anatomical feature.

In step 316, the generated images may be displayed.

In optional step 318, input/output may be configured and/or managed during display of images based on the identified anatomical feature (e.g., scaling, description of particular details, etc.).

Figure 4:
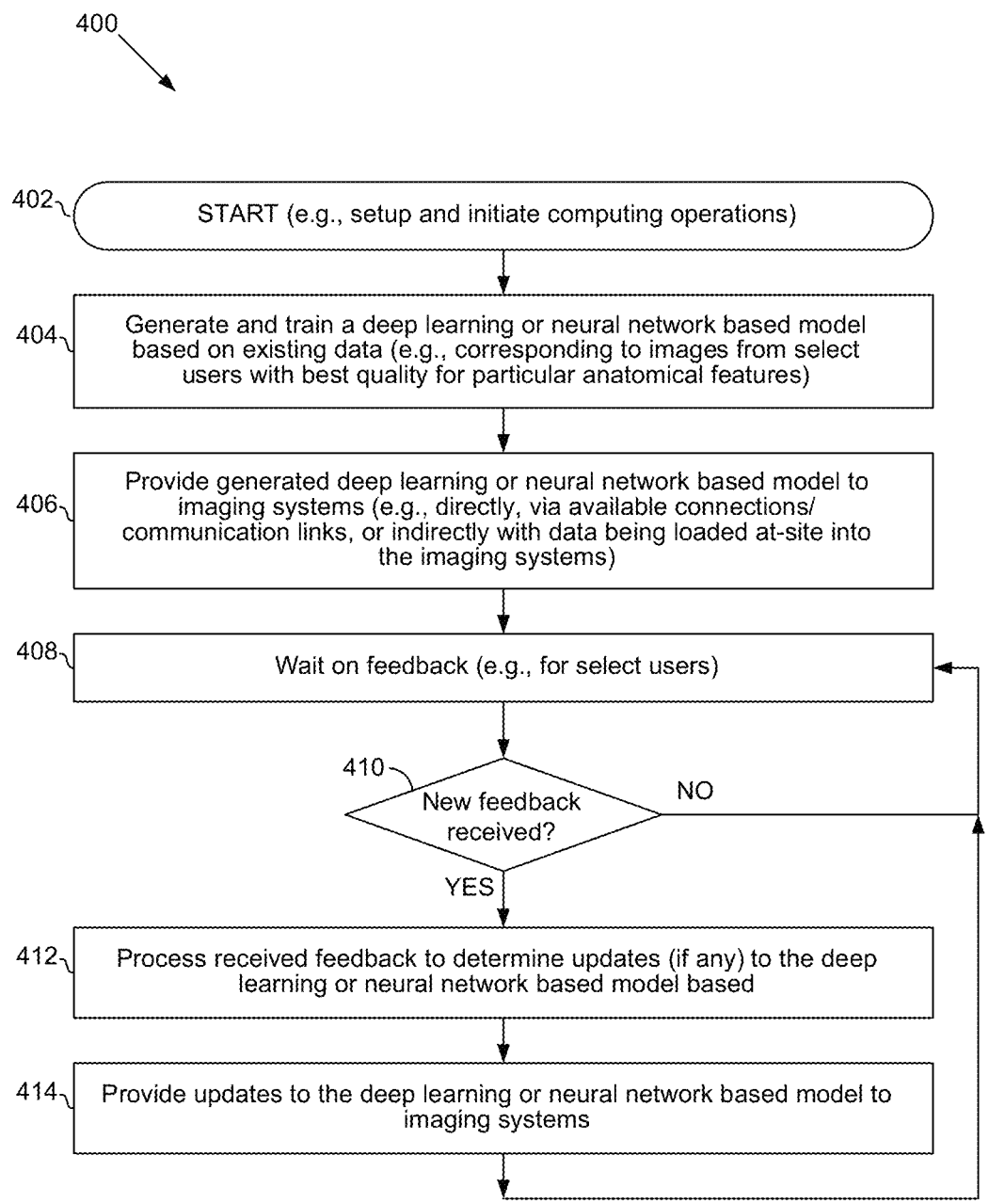
FIG. 4 illustrates a flowchart of an example steps that may be performed for generating and updating control data for automated organ recognition and image optimization.

FIG. 4 illustrates a flowchart of an example steps that may be performed for generating and updating control data for automated organ recognition and image optimization.

Shown in FIG. 4 is flow chart 400, comprising a plurality of example steps (represented as blocks 402-414), which may be performed in a suitable system (e.g., computing system 120 of FIG. 1) to generate and update control data for automated organ recognition and image optimization.

In start step 402, the system may be setup, and operations may initiate.

In step 404, a deep learning or neural network based model may be generated and/or trained, such as based on existing data (e.g., corresponding to images from select users with best quality for particular anatomical features).

In step 406, the generated deep learning or neural network based model may be provided to imaging systems (e.g., directly, via available connections/communication links, or indirectly with data being loaded at-site into the imaging systems.

In step 408, the process may continually wait on feedback (e.g., from select user, such as "experts"), and when it is determined in step 410 that no new feedback is received, the process loops back to step 408. When it is determined in step 410 that new feedback is received, the process proceeds to step 412.

In step 412, the received new feedback may be processed, to determine updates (if any) to the deep learning or neural network based model based.

In step 414, the updates to the deep learning or neural network based model are provided to imaging systems.

As utilized herein the terms "circuits" and "circuitry" refer to physical electronic components (e.g., hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. In other words, "x and/or y" means "one or both of x and y." As another example, "x, y, and/or z" means any element of the seven-element set {(x), (y), (z), (x, y), (x, z), (y, z), (x, y, z)}. In other words, "x, y and/or z" means "one or more of x, y, and z." As utilized herein, the terms "block" and "module" refer to functions than can be performed by one or more circuits. As utilized herein, the term "exemplary" means serving as a non-limiting example, instance, or illustration. As utilized herein, the terms "for example" and "e.g.," set off lists of one or more non-limiting examples, instances, or illustrations. As utilized herein, circuitry is "operable" to perform a function whenever the circuitry comprises the necessary hardware (and code, if any is necessary) to perform the function, regardless of whether performance of the function is disabled or not enabled (e.g., by some user-configurable setting, a factory trim, etc.).

Other embodiments of the invention may provide a non-transitory computer readable medium and/or storage medium, and/or a non-transitory machine readable medium and/or storage medium, having stored thereon, a machine code and/or a computer program having at least one code section executable by a machine and/or a computer, thereby causing the machine and/or computer to perform the processes as described herein.

Accordingly, the present disclosure may be realized in hardware, software, or a combination of hardware and software. The present invention may be realized in a centralized fashion in at least one computing system, or in a distributed fashion where different elements are spread across several interconnected computing systems. Any kind of computing system or other apparatus adapted for carrying out the methods described herein is suited. A typical combination of hardware and software may be a general-purpose computing system with a program or other code that, when being loaded and executed, controls the computing system such that it carries out the methods described herein. Another typical implementation may comprise an application specific integrated circuit or chip.

Various embodiments in accordance with the present disclosure may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

What is claimed is:

1. A method, comprising:
   in a medical imaging device:
   automatically identifying, during medical imaging based on an imaging technique, an anatomical feature in an area being imaged;
   automatically determining, based on said identifying of said anatomical feature, one or more imaging parameters or settings for optimizing imaging quality for said anatomical feature;
   configuring without any input or action by a user of said medical imaging device, imaging functions applied in said medical imaging device during imaging operations, based on said one or more imaging parameters or settings;
   acquiring based on said configuring of said imaging functions, medical imaging dataset corresponding to said area being imaged; and
   generating, based on processing of said medical imaging dataset, one or more medical images for rendering.

2. The method of claim 1, comprising identifying said anatomical feature and determining said one or more imaging parameters or settings using a deep learning and/or neural network based model.

3. The method of claim 2, wherein said deep learning and/or neural network based model is pre-trained for recognizing one or more anatomical features.

4. The method of claim 2, wherein said deep learning and/or neural network based model is pre-trained for selecting, for each recognized anatomical feature, one or more imaging optimization parameters or settings.

5. The method of claim 2, wherein said deep learning and/or neural network based model is generated and/or updated based on feedback data from one or more users, said feedback data relating to recognizing and/or optimizing imaging for anatomical features.

6. The method of claim 5, wherein at least some of said feedback data is collected and processed in a dedicated computing system.

7. The method of claim 6, wherein said deep learning and/or neural network based model and/or updates to said deep learning and/or neural network based model are imported from said dedicated computing system to said medical imaging device.

8. The method of claim 1, comprising configuring handling of user input and/or output, during said medical imaging, based on said identifying of said anatomical feature.

9. The method of claim 1, comprising incorporating into said one or more medical images, based on said identifying of said anatomical feature, information relating to said anatomical feature.

10. The method of claim 1, wherein:
    said imaging technique comprises ultrasound imaging; and
    said medical imaging dataset is acquired using captured echo ultrasound signals.

11. A system, comprising:
    a probe that is operable to acquire medical imaging data;
    a control component that comprises processing circuitry; and
    an input/output component for outputting medical images;

wherein said processing circuitry is operable to:
> automatically identify, during medical imaging based on an imaging technique, an anatomical feature in an area being imaged;
> automatically determine, based on said identifying of said anatomical feature, one or more imaging parameters or settings for optimizing imaging quality for said anatomical feature;
> configure without any input or action by a user of the system, imaging related functions applied in said system during imaging operations, based on said one or more imaging parameters or settings; and
> generate, based on processing on medical imaging dataset acquired via said probe, one or more medical images for rendering via said input/output component.

12. The system of claim 11, wherein said processing circuitry is operable to identify said anatomical feature and determine said one or more imaging parameters or settings using a deep learning and/or neural network based model.

13. The system of claim 12, wherein said deep learning and/or neural network based model is pre-trained for recognizing one or more anatomical features.

14. The system of claim 12, wherein said deep learning and/or neural network based model is pre-trained for selecting, for each recognized anatomical feature, one or more imaging optimization parameters or settings.

15. The system of claim 12, wherein said deep learning and/or neural network based model is configured and/or updated based on feedback data from one or more users, said feedback data relating to recognizing and/or optimizing imaging for anatomical features.

16. The system of claim 12, wherein said deep learning and/or neural network based model and/or updates to said deep learning and/or neural network based model are imported into said system.

17. The system of claim 11, wherein said processing circuitry is operable to handle user input and/or output, during said medical imaging, based on said identifying of said anatomical feature.

18. The system of claim 11, wherein said processing circuitry is operable to incorporate into said one or more medical images, based on said identifying of said anatomical feature, information relating to said anatomical feature.

19. The system of claim 11, wherein:
> said imaging technique comprises ultrasound imaging; and
> said medical imaging dataset is acquired using captured echo ultrasound signals.

20. A non-transitory computer readable medium having stored thereon, a computer program having at least one code section, the at least one code section being executable by a machine for causing the machine to perform one or more steps comprising:
> automatically identifying, during medical imaging based on an imaging technique, an anatomical feature in an area being imaged based on a deep learning and/or neural network based model;
> automatically determining, based on said identifying of said anatomical feature, and using said deep learning and/or neural network based model, one or more imaging parameters or settings for optimizing imaging quality for said anatomical feature;
> configuring without any input or action by a user of said machine, operations and/or functions applied in said machine during said medical imaging based on said one or more imaging parameters or settings;
> acquiring based on said configuring of said operations and/or functions, medical imaging datasets corresponding to said area being imaged; and
> generating, based on processing on said medical imaging datasets, one or more medical images for rendering.

* * * * *